United States Patent [19]

Takemoto

[11] Patent Number: 4,563,535
[45] Date of Patent: Jan. 7, 1986

[54] PROCESS FOR PRODUCING TETRAHYDROPHTHALIMIDES

[75] Inventor: Ichiki Takemoto, Toyonaka, Japan

[73] Assignee: Sumitomo Chemical Co., Ltd., Osaka, Japan

[21] Appl. No.: 649,698

[22] Filed: Sep. 12, 1984

[30] Foreign Application Priority Data

Sep. 19, 1983 [JP] Japan .................. 58-173891
Sep. 21, 1983 [JP] Japan .................. 58-175486
Sep. 21, 1983 [JP] Japan .................. 58-175489
Sep. 21, 1983 [JP] Japan .................. 58-175490
Sep. 21, 1983 [JP] Japan .................. 58-175491
Sep. 21, 1983 [JP] Japan .................. 58-175492

[51] Int. Cl.[4] .................. C07D 209/48; A01N 43/38
[52] U.S. Cl. .................. 548/513; 548/514; 71/96
[58] Field of Search .................. 548/513, 514

[56] References Cited

U.S. PATENT DOCUMENTS

| 4,006,185 | 2/1977 | Tobin et al. | 564/442 |
| 4,292,070 | 9/1981 | Wakabayashi et al. | 548/513 |
| 4,431,822 | 2/1984 | Nagano et al. | 548/513 |

FOREIGN PATENT DOCUMENTS 0061741 3/1982 European Pat. Off.
0083055 12/1982 European Pat. Off.

OTHER PUBLICATIONS

Bil, Methods, *Apparatus: New Product Research, Process Development and Design* Chemistry and Industry 198 (1969).
Koga et al., *Structure–Activity Relationships of Antibacterial 6,7- and 7,8 Disubstituted 1-Alkyl-1,4-Dihydro-4-Oxoquinoline-3-Carboxylic Acids*, Journal of Medical Chemistry, 1980, 1358–1363.

*Primary Examiner*—John Kight
*Assistant Examiner*—Marvin L. Moore
*Attorney, Agent, or Firm*—Birch, Stewart, Kolasch & Birch

[57] ABSTRACT

A compound of the formula:

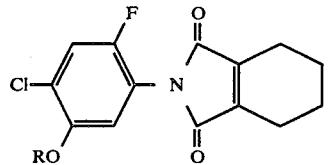

wherein R is an isoproyl group or an n-amyloxycarbonylmethyl group, useful as a herbicide, is effectively produced by reacting a compound of the formula:

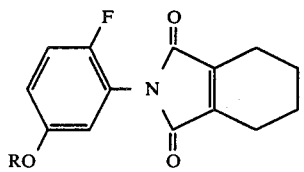

wherein R is as defined above, with sulfuryl chloride or chlorine in a solvent in the presence of a dehydrohalogenating agent.

13 Claims, No Drawings

PROCESS FOR PRODUCING TETRAHYDROPHTHALIMIDES

The present invention relates to a process for producing tetrahydrophthalimides. More particularly, it relates to a process for producing N-(5-substituted-4-chloro-2-fluorophenyl)-3,4,5,6-tetrahydrophthalimides of the formula:

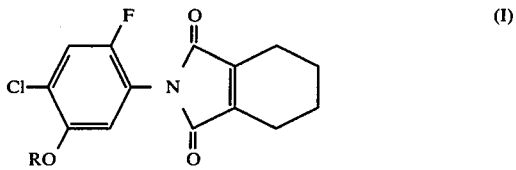

wherein R is an isopropyl group or an n-amyloxycarbonyl-methyl group.

It is known that certain kinds of tetrahydrophthalimides are effective as herbicides. For instance, U.S. Pat. No. 4,431,822 and EP-0083055A disclose respectively N-(4-chloro-2-fluoro-5-isopropoxyphenyl)-3,4,5,6-tetrahydrophthalimide and N-(4-chloro-2-fluoro-5-n-amyloxycarbonylmethoxyphenyl)-3,4,5,6-tetrahydrophthalimide, which are useful as herbicides. For production of those tetrahydrophthalimides, 4-chloro-2-fluoro-5-isopropoxyaniline or 4-chloro-2-fluoro-5-n-amyloxycarbonylmethoxyaniline is reacted with 3,4,5,6-tetrahydrophthalic acid anhydride. However, this process requires a lot of steps with troublesome operations for preparation of the starting 4-chloro-2-fluoro-5-isopropoxyaniline or 4-chloro-2-fluoro-5-n-amyl-carbonylmethoxyaniline and is therefore hardly applicable in an industrial scale.

As a result of the extensive study for production of the tetrahydrophthalimides (I) in an industrially advantageous manner, it has been found that chlorination of N-(2-fluoro-5-isopropoxyphenyl)-3,4,5,6-tetraphthalimide or N-(2-fluoro-5-n-amyloxycarbonylmethoxyphenyl)-3,4,5,6-tetraphthalimide, affords the objective and corresponding tetrahydrophthalimide (I) in a high yield and with a high purity. The present invention is based on this finding.

According to this invention, there is provided a process for producing the tetrahydrophthalimide of the formula (I) which comprises reacting the corresponding N-(5-substitited-2-fluorophenyl)-3,4,5,6-tetrahydrophthalimide of the formula:

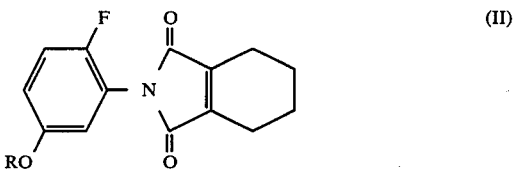

wherein R is as defined above with sulfuryl chloride or chlorine in a solvent in the presence of a dehydrohalogenating agent at a temperature of 10° to 100° C. for a period of 1 to 10 hours.

The amounts of sulfuryl chloride or chlorine and of the dehydrohalogenating agent may be respectively from 1 to 7 equivalents and from 0.0001 to 1 equivalent to the starting compound (II).

Examples of the solvent usable in the reaction are aliphatic hydrocarbons (e.g. hexane, heptane, ligloin, petroleum ether), halogenated hydrocarbons (e.g. chloroform, carbon tetrachloride, dichloroethane, chlorobenzene, dichlorobenzene, trichloroethylene, tetrachloroethylene), ethers (e.g. diethyl ether, diisopropyl ether, dioxane, tetrahydrofuran, ethylene glycol dimethyl ether), esters (e.g. ethyl acetate, butyl acetate), nitro compounds (e.g. nitrobenzene), tertiary amines (e.g. pyridine, triethylamine, tributylamine), acid amides (e.g. N,N-dimethylformamide), sulfur compounds (e.g. dimethylsulfoxide, sulforane), rane), etc. These may be used alone or in combination.

As the dehydrohalogenating agent, there may be exemplified an organic base (e.g. pyridine, triethylamine, N,N-diethylaniline, dicyclohexylamine), an inorganic base (e.g. sodium hydroxide, potassium hydroxide, sodium carbonate, potassium carbonate), etc.

After completion of the reaction, the reaction mixture may be subjected to ordinary post-treatment such as extraction with an organic solvent or concentration to obtain the objective tetrahydrophthalimide (I). If necessary, purification by chromatography or recrystallization may be adopted.

The N-(5-substituted-2-fluorophenyl)-3,4,5,6-tetrahydrophthalimide (II) as the starting compound may be prepared, for instance, according to the following scheme:

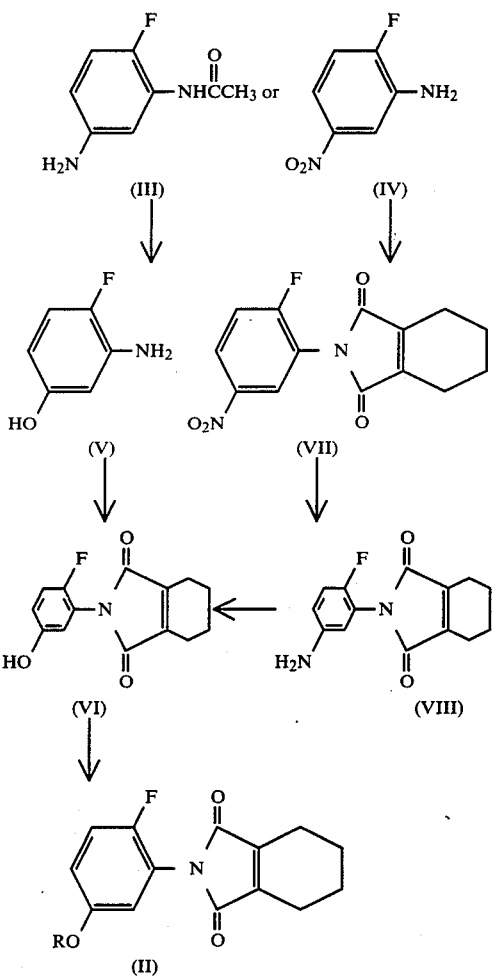

wherein R is as defined above.

With reference to the above scheme, production of the N-(5-substituted-2-fluorophenyl)-3,4,5,6-tetrahydrophthalimide (II) will be hereinafter explained in detail.

(a) Production of the N-(5-substituted-2-fluorophenyl)-3,4,5,6-tetrahydrophthalimide (II):

The compound (II) is obtainable by reacting N-(2-fluoro-5-hydroxyphenyl)-3,4,5,6-tetrahydrophthalimide (VI) with a halide of the formula:

wherein X is a chlorine atom, a bromine atom or an iodine atom and R is as defined above in a solvent in the presence of a dehydrohalogenating agent, if necessary, in the presence of potassium iodide, at a temperature of 50° to 150° C. for a period of 0.5 to 10 hours.

In the reaction, the halide (IX) and the dehydrohalogenating agent may be respectively used in amounts of 1 to 2 equivalents to the compound (VI). As the solvent, there are exemplified aliphatic hydrocarbons (e.g. hexane), aromatic hydrocarbons (e.g. benzene, toluene, xylene), halogenated hydrocarbons (e.g. chlorobenzene, dichlorobenzene,), ethers (e.g. dioxane, tetrahydrofuran, ethylene glycol dimethyl ether), ketones (e.g. acetone, methyl ethyl ketone, methyl isobutyl ketone, isophorone, cyclohexanone), esters (e.g. ethyl acetate, butyl acetate), nitro compounds (e.g. nitrobenzene), nitriles (e.g. acetonitrile, isobutyronitrile), tertiary amines (e.g. pyridine, triethylamine, N,N-diethylaniline, tributylamine), acid amides (e.g. N,N-dimethylformamide), sulfur compounds (e.g. dimethylsulfoxide, sulforane), water, etc. Examples of the dehydrohalogenating agent are organic bases (e.g. pyridine, triethylamine, N,N-diethylaniline), inorganic bases (e.g. sodium hydroxide, potassium hydroxide, sodium carbonate, potassium carbonate), etc.

After completion of the reaction, the reaction mixture may be subjected to ordinary post-treatment such as extraction with an organic solvent or concentration to obtain the compound (II). If necessary, purification by chromatography or recrystallization may be adopted.

(b) Production of N-(2-fluoro-5-hydroxyphenyl)-3,4,5,6-tetrahydrophthalimide (VI) from 3-amino-4-fluorophenol (V):

The compound (VI) is obtainable by reacting the compound (V) with a 1 to 1.5 equivalent amount of 3,4,5,6-tetrahydrophthalic anhydride in a solvent at a temperature of 100° to 120° C. for a period of 1 to 10 hours. The solvent usable in the reaction may be chosen from aliphatic acids (e.g. acetic acid), acid amides (e.g. N,N-dimethylformamide), sulfur compounds (e.g. dimethylsulfoxide, sulforane), water, etc.

After completion of the reaction, the reaction mixture may be subjected to ordinary post-treatment such as extraction with an organic solvent or concentration to obtain the compound (VI). If necessary, purification by chromatography or recrystallization may be adopted.

The compound (V), i.e. 3-amino-4-fluorophenol, is known and may be prepared according to the procedure as described in U.S. Pat. No. 4,006,185. However, it can be efficiently produced by the procedure as set forth below.

(c) Production of 3-amino-4-fluorophenol (V):

2-Fluoro-5-aminoacetoanilide (III) is reacted with a 1 to 2 equivalent amount of sodium nitrite in a solvent (e.g. sulfuric acid, hydrochloric acid, water) at a temperature of 0° to 20° C. for a period of 5 minutes to 5 hours to give its diazonium salt, followed by hydrolyzing the diazonium salt in dilute sulfuric acid at a temperature of 90° to 180° C. The reaction mixture after hydrolysis is adjusted to pH 4 to 7 with addition of an alkali such as sodium hydroxide and subjected to post-treatment such as extraction with an organic solvent or concentration to obtain the compound (V). If necessary, purification by chromatography or recrystallization may be adopted.

The compound (III), i.e. 2-fluoro-5-aminoacetoanilide, is known and may be prepared according to the procedure as described in J. Med. Chem., 1980, 1358–1363.

(d) Production of N-(2-fluoro-5-hydroxyphenyl)3,4,5,6-tetrahydrophthalimide (VI) from N-(2-fluoro-5-aminophenyl)-3,4,5,6-tetrahydrophthalimide (VIII):

The compound (VI) is prepared by reacting the compound (VIII) with a 1 to 2 equivalent amount of sodium nitrite in a solvent (e.g. sulfuric acid, hydrochloric acid, acetic acid, water) at a temperature of 0° to 20° C. for a period of 5 minutes to 5 hours to obtain its diazonium salt, followed by hydrolysis of the diazonium salt in dilute sulfuric acid at a temperature of 20° to 100° C. In the hydrolysis, a copper compound such as cuprous oxide or cupric nitrate may be used in place of dilute sulfuric acid.

(e) Production of N-(2-fluoro-5-aminophenyl)-3,4,5,6-tetrahydrophthalimide (VIII):

The compound (VIII) is prepared by reacting the compound (VII), i.e. N-(2-fluoro-5-nitrophenyl)-3,4,5,6-tetrahydrophthalimide, with a 2 to 5 equivalent amount of iron powders (e.g. reduced iron, electrolytic iron) in a solvent in the presence of a catalytic amount of an acid (e.g. hydrochloric acid, sulfuric acid, acetic acid) at a temperature of 90° to 120° C. for a period of 1 to 10 hours.

Alternatively, the compound (VII) is subjected to catalytic reduction in the presence of a catalyst (e.g. platinum dioxide) in a solvent at room temperature under atmospheric pressure for a period of 1 to 10 hours to give the compound (VIII).

Examples of the solvent usable in the reaction as above are aliphatic hydrocarbons (e.g. hexane), aromatic hydrocarbons (e.g. benzene, toluene, xylene), ethers (e.g. dioxane, ethylene glycol dimethyl ether), fatty acids (e.g. acetic acid), alcohols (e.g. methanol, ethanol, isopropanol, t-butanol, octanol, cyclohexanol, methylcellosolve, diethylene glycol, glycerin), esters (e.g. ethyl acetate, butyl acetate), water, etc. These solvents may be used alone or in combination.

After completion of the reaction, the reaction mixture may be subjected to post-treatment such as removal of the reducing agent or the catalyst, extraction with an organic solvent or concentration to obtain the compound (VIII). If necessary, purification by chromatography or recrystallization may be adopted.

(f) Production of N-(2-fluoro-5-nitrophenyl)-3,4,5,6-tetrahydrophthalimide (VII):

The compound (VII) is obtainable by reacting the compound (IV), i.e. 2-fluoro-5-nitroaniline, with a 1 to 1.2 equivalent amount of 3,4,5,6-tetrahydrophthalic anhydride in a solvent at a temperatursе of 100° to 120° C. for a period of 1 to 10 hours.

As the solvent, there may be exemplified fatty acids (e.g. acetic acid), acid amides (e.g. N,N-dimethylformamide), sulfur compounds (e.g. dimethylsulfoxide, sulforane), water, etc. These may be used alone or in combination.

After completion of the reaction, the reaction mixture may be subjected to post-treatment such as extraction with an organic solvent or concentration to obtain the compound (VII). If necessary, purification by chromatography or recrystallization may be adopted.

The compound (IV) is per se known and may be prepared by the procedure as described in Chemistry and Industry, 198 (1969).

In addition, the compounds (II), (VI), (VII) and (VIII) are novel, and these may be represented by the following general formula:

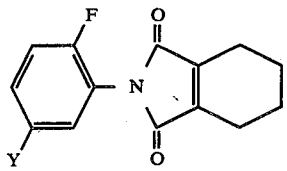

(X)

wherein Y is an isopropoxy group, an n-amyloxycarbonylmethoxy group, a hydroxyl group, a nitro group or an amino group.

Practical and presently preferred embodiments of the invention are illustratively shown in the following examples.

EXAMPLE 1

Preparation of N-(4-chloro-2-fluoro-5-isopropoxyphenyl)-3,4,5,6-tetrahydrophthalimide (I: R=isopropyl):

N-(2-Fluoro-5-isopropoxyphenyl)-3,4,5,6-tetrahydrophthalimide (II: R=isopropyl) (2 g) and dicyclohexylamine (0.01 g) were dissolved in tetrachloroethylene (20 ml), and a solution of sulfuryl chloride (1 g) in tetrachloroethylene (5 ml) was added dropwise thereto at 80° C. in 2 hours. After completion of the addition, the resultant mixture was stirred at the same temperature as above for 2 hours, followed by extraction with ethyl acetate. The extract was concentrated, and the precipitated crystals were collected by filtration to give 1.85 g of N-(4-chloro-2-fluoro-5-isopropoxyphenyl)-3,4,5,6-tetrahydrophthalimide (I: R=isopropyl). M.P., 81°-82° C.

EXAMPLE 2

Preparation of N-(4-chloro-2-fluoro-5-isopropoxyphenyl)-3,4,5,6-tetrahydrophthalimide (I: R=isopropyl):

N-(2-Fluoro-5-isopropoxyphenyl)-3,4,5,6-tetrahydrophthalimide (II: R=isopropyl) (1 g) and dicyclohexylamine (0.01 g) were dissolved in tetrachloroethylene (20 ml), and chlorine (1 ml) was introduced therein at room temperature. The resultant solution was stirred at the room temperature for 2 hours. The reaction mixture was extracted with methylene chloride, and the extract was concentrated. The residue was purified by silica gel chromatography using a mixture of n-hexane and ethyl acetate as an eluent to give 0.9 g of N-(4-chloro-2-fluoro-5-isopropoxyphenyl)-3,4,5,6-tetrahydrophthalimide (I: R=isopropyl). M.P., 81°-82° C.

EXAMPLE 3

Preparation of N-(4-chloro-2-fluoro-5-n-amyloxycarbonylmethoxyphenyl)-3,4,5,6-tetrahydrophthalimide (I: R=n-amyloxycarbonylmethyl):

N-(2-Fluoro-5-n-amyloxycarbonylmethoxyphenyl)-3,4,5,6-tetrahydrophthalimide (II: R=n-amyloxycarbonylmethyl) (2 g) and dicyclohexylamine (0.01 g) were dissolved in tetrachloroethylene (10 g) and kept at 80° C. A solution of sulfuryl chloride (2.6 g) in tetrachloroethylene (7.8 g) was dropwise added thereto at 80°-83° C. in 5 hours, and the resultant mixture ws stirred at 80°-82° C. for 1.5 hours. After being allowed to cool, the reaction mixture was poured into water and extracted with ethyl acetate. The extract was concentrated under reduced pressure to give 2.0 g of N-(4-chloro-2-fluoro-5-n-amyloxycarbonylmethoxyphenyl-3,4,5,6-tetrahydrophthalimide (I: R=n-amyloxycarbonylmethyl). M.P., 90°-91° C.

EXAMPLE 4

Preparation of N-(2-fluoro-5-isopropoxyphenyl)3,4,5,6-tetrahydrophthalimide (II: R=isopropyl)

N-(2-Fluoro-5-hydroxyphenyl)-3,4,5,6-tetrahydrophthalimide (VI) (10 g), isopropyl iodide (7 g) and anhydrous potassium carbonate (5.2 g) were dissolved in acetonitrile (100 ml), and the resultant solution was heated under reflux for 2.5 hours. After cooling, the reaction mixture was extracted with ethyl acetate. The extract was concentrated, and the precipitated crystals were collected by filtration to give 9 g of N-(2-fluoro-5-isopropoxyphenyl)-3,4,5,6-tetrahydrophthalimide (II: R=isopropyl). M.P. 62.8° C.

EXAMPLE 5

Preparation of N-(2-fluoro-5-isopropoxyphenyl)-3,4,5,6-tetrahydrophthalimide (II: R=isopropyl)

N-(2-Fluoro-5-hydroxyphenyl)-3,4,5,6-tetrahydrophthalimide (VI) (20 g), isopropyl bromide (25 g), potassium iodide (5 g) and anhydrous potassium carbonate (11 g) were dissolved in a mixture of acetonitrile (135 g) and dimethylformamide (15 g), and the resultant solution was heated under reflux for 7 hours. After cooling, the reaction mixture was extracted with ethyl acetate. The extract was concentrated, and the precipitated crystals were collected by filtration to give 23.2 g of N-(2-fluoro-5-isopropoxyphenyl)-3,4,5,6-tetrahydrophthalimide (II: R=isopropyl). M.P. 62.8° C.

EXAMPLE 6

Preparation of N-(2-fluoro-5-n-amyloxycarbonylmethoxyphenyl)-3,4,5,6-tetrahydrophthalimide (II: R=n-amyloxycarbonylmethyl):

N-(2-Fluoro-5-hydroxyphenyl)-3,4,5,6-tetrahydrophthalimide (VI) (9 g), n-amyl chloroacetate (8 g) and potassium carbonate (6.7 g) were dissolved in a mixture of acetonitrile (50 ml) and dimethylformamide (10 ml), and the resultant mixture was heated under reflux for 6 hours. After cooling, the reaction mixture was diluted with water and extracted with ethyl acetate. The solvent was removed under reduced pressure to give 12 g of N-(2-fluoro-5-n-amyloxycarbonylmethoxyphenyl)-

3,4,5,6-tetrahydrophthalimide (II: R=n-amyloxycarbonylmethyl). $n_D^{25}$ 1.5218.

EXAMPLE 7

Preparation of N-(2-fluoro-5-hydroxyphenyl)-3,4,5,6-tetrahydrophthalimide (VI)

3-Amino-4-fluorophenol (V) (2 g) and 3,4,5,6-tetrahydrophthalic anhydride (2.4 g) were dissolved in acetic acid (50 ml), and the resultant solution was heated under reflux for 1hour, followed by extraction with ethyl acetate. The extract was concentrated, and the precipitated crystals were collected by filtration and washed with a small amount of ether to give 3.3 g of N-(2-fluoro-5-hydroxyphenyl)-3,4,5,6-tetrahydrophthalimide (VI). M.P. 164.6° C.

EXAMPLE 8

Preparation of N-(2-fluoro-5-hydroxyphenyl)-3,4,5,6-tetrahydrophthalimide (VI):

To N-(2-fluoro-5-aminophenyl)-3,4,5,6-tetrahydrophthalimide (VII) (2.6 g), acetic acid (26 g) and conc. sulfuric acid (2.5 g) were added, and the resultant mixture was kept at a temperature below 10° C. A solution of sodium nitrite (1.0 g) in water (10 g) was added dropwise thereto at a temperature of 5° to 10° C. The resulting mixture was stirred for 15 minutes, followed by decomposition of excess of sodium nitrite with urea (0.3 g). A solution of cupric nitrate (38.6 g) in water (100 g) was added dropwise thereto at room temperature. After addition of cuprous oxide (1.5 g), the resultant mixture was stirred vigorously at room temperature for 10 minutes. The reaction mixture was extracted with ethyl acetate, and the solvent was removed by distillation under reduced pressure. The residue was purified by silica gel chromatography using a mixture of n-hexane and ethyl acetate as an eluent to give 0.7 g of N-(2-fluoro-5-hydroxyphenyl)-3,4,5,6-tetrahydrophthalimide (VI). M.P., 164.6° C. M.P., 164.6° C.

EXAMPLE 9

Preparation of 3-amino-4-fluorophenol (V)

2-Fluoro-5-aminoacetoanilide (III) (20 g) was added to a mixture of water (36 ml), conc. sulfuric acid (26 ml) and ice-water (64 ml), and the resultant mixture was stirred under ice-cooling. A solution of sodium nitrite (8.4 g) in water (20 ml) was added dropwise thereto at a temperature below 5° C. After completion of the addition, the mixture was stirred at a temperature below 5° C. for 5 minutes to produce the diazonium salt. The resultant mixture containing the diazonium salt was added to dilute sulfuric acid (obtained from conc. sulfuric acid (80 ml) and water (60 ml)) under reflux, and heating with reflux was continued for 5 minutes. The reaction mixture was allowed to cool, and 30% aqueous sodium hydroxide solution was added thereto, whereby the pH was adjusted to 4. The resulting mixture was extracted with ethyl acetate, and the extract was concentrated. The precipitated crystals were collected by filtration to give 12.9 g of 3-amino-4-fluorophenol (V). M.P. 137°-139° C.

EXAMPLE 10

Preparation of N-(2-fluoro-5-aminophenyl)-3,4,5,6-tertrahydrophthalimide (VIII)

N-(2-Fluoro-5-nitrophenyl)-3,4,5,6-tetrahydrophthalimide (VII) (5 g) and platinum dioxide (0.2 g) were suspended in ethyl acetate (50 ml), and the resultant suspension was allowed to catalytic reduction at room temperature under atmospheric pressure until 1.3 liters of hydrogen was taken up. The reaction mixture was filtered and concentrated to give 4.48 g of N-(2-fluoro-5-aminophenyl)-3,4,5,6-tetrahydrophthalimide (VIII). M.P., 117°-119° C.

EXAMPLE 11

Preparation of N-(2-fluoro-5-aminophenyl)-3,4,5,6-tetrahydrophthalimide (VIII)

To a suspension of electrolytic iron powders (9 g) in 5% acetic acid (200 g) under reflux, a solution of N-(2-fluoro-5-nitrophenyl)-3,4,5,6-tetrahydrophthalimide (VII) (15 g) in acetic acid (50 g) was added dropwise. After completion of the addition, the resultant mixture was heated under reflux for 30 minutes, cooled and filtered. The filtrate was diluted with water and extracted with ethyl acetate. The extract was concentrated, and the precipitated crystals were collected by filtration to give 10.5 g of N-(2-fluoro-5-aminophenyl)-3,4,5,6-tetrahydrophthalimide (VIII). M.P., 117°-119° C.

EXAMPLE 12

Preparation of N-(2-fluoro-5-nitrophenyl)-3,4,5,6-tetrahydrophthalimide (VII):

2-Fluoro-5-nitroaniline (IV) (50 g) and 3,4,5,6-tetrahydrophthalic anhydride (49 g) were dissolved in acetic acid (200 ml), and the resultant solution was heated under reflux for 4 hours. After cooling, the reaction mixture was diluted with water and extracted with ethyl acetate. The extract was concentrated, and the precipitated crystals were collected by filtration to give 72 g of N-(2-fluoro-5-nitrophenyl)-3,4,5,6-tetrahydrophthalimide (VII). M.P., 154.9° C.

What is claimed is:

1. A process for producing a tetrahydrophthalimide of the formula:

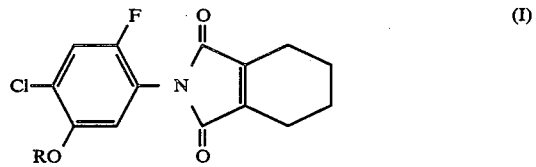

(I)

wherein R is an isopropyl group or an n-amyloxycarbonylmethyl group, which comprises reacting N-(5-substituted-2-fluorophenyl)-3,4,5,6-tetrahydrophthalimide of the formula:

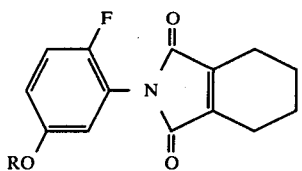

(II)

wherein R is as defined above with sulfuryl chloride or chlorine in a solvent in the presence of a dehydrohalogenating agent.

2. The process according to claim 1, wherein the reaction is carried out at a temperature of 10° to 100° C.

3. The process according to claim 1, wherein the sulfuryl chloride or chlorine is used in an amount of 1 to 7 equivalents based on the starting N-(5-substituted-2-fluorophenyl)-3,4,5,6-tetrahydrophthalimide.

4. The process according to claim 1, wherein the dehydrohalogenating agent is used in an amount of 0.001 to 1 equivalents based on the starting N-(5-substituted-2-fluorophenyl)tetrahydrophthalimide.

5. The process according to claim 1, wherein the dehydrohalogenating agent is an organic base or an inorganic base.

6. The process according to claim 5, wherein the organic base is pyridine, triethylamine, N,N-diethylaniline or dicyclohexylamine.

7. The process according to claim 5, wherein the inorganic base is sodium hydroxide, potassium hydroxide, sodium carbonate or potassium carbonate.

8. The process according to claim 1, wherein the N-(5-substituted-2-fluorophenyl)-3,4,5,6-tetrahydrophthalimide is the one produced by reacting N-(2-fluoro-5-hydroxyphenyl)-3,4,5,6-tetrahydrophthalimide with a halide of the formula:

R—X wherein R is as defined in claim 1 and X is a chlorine atom, a bromine atom or an iodine atom.

9. The process according to claim 8, wherein the N-(2-fluoro-5-hydroxyphenyl)-3,4,5,6-tetrahydrophthalimide is the one produced by (a) reacting 3-amino-4-fluorophenol with 3,4,5,6-tetrahydrophthalic anhydride, or (b) reacting N-(2-fluoro-5-aminophenyl)-3,4,5,6-tetrahydrophthalimide with sodium nitrite to make the diazonium salt and hydrolyzing the resulting diazonium salt.

10. The process according to claim 9, wherein 3-amino-4-fluorophenol is the one produced by reacting 2-fluoro-5-aminoacetanilide with sodium nitrite to make the diazonium salt and hydrolyzing the resulting diazonium salt.

11. The process according to claim 9, wherein N-(2-fluoro-5-aminophenol)-3,4,5,6-tetrahydrophthalimide is the one produced by reducing N-(2-fluoro-5-nitrophenyl)-3,4,5,6-tetrahydrophthalimide.

12. The process according to claim 11, wherein N-(2-fluoro-5-nitrophenyl)-3,4,5,6-tetrahydrophthalimide is the one produced by reacting 2-fluoro-5-nitroaniline with 3,4,5,6-tetrahydrophthalic anhydride.

13. A compound of the formula:

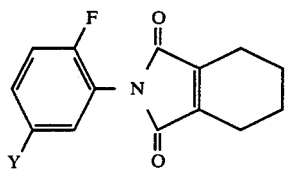

wherein Y is an isopropoxy group, an n-amyloxycarbonylmethoxy group, a hydroxyl group, a nitro group or an amino group.

* * * * *